(12) United States Patent
Simard et al.

(10) Patent No.: US 9,080,952 B2
(45) Date of Patent: Jul. 14, 2015

(54) METHOD AND A DEVICE OF PHASED ARRAY INSPECTION WITH PULSE RATE OPTIMIZATION

(75) Inventors: Christian Simard, Quebec City (CA); Denys Laquerre, St-Augustine de-Desmaures (CA)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 597 days.

(21) Appl. No.: 13/360,175

(22) Filed: Jan. 27, 2012

(65) Prior Publication Data

US 2013/0197841 A1    Aug. 1, 2013

(51) Int. Cl.
*G01N 29/26*    (2006.01)
*G01N 29/34*    (2006.01)

(52) U.S. Cl.
CPC ............ *G01N 29/262* (2013.01); *G01N 29/343* (2013.01)

(58) Field of Classification Search
CPC ... G01N 29/262; G01N 29/00; G01N 29/028; G01N 29/09; G01N 29/24; G01N 29/34; G01N 29/343
USPC ........... 702/33–36, 39, 57, 64–67, 70–73, 75, 702/81, 84–85, 104–108, 113, 116–117, 702/124, 126–127, 176, 182–183, 185, 702/188–189; 324/76.12, 500, 537, 324/600–603, 605, 609; 367/13, 140
See application file for complete search history.

(56) References Cited

U.S. PATENT DOCUMENTS

2010/0327880 A1*  12/2010  Stein ............................ 324/639

OTHER PUBLICATIONS

Svilainis et al., Measurement of Complex Impedance of Ultrasonic Transducers, 2007, Ultragarsas, Nr. 1(62), pp. 26-29.*
Svilainis et al., Evaluation of the Ultrasonic Transducer Electrical Matching Performance, 2007, Ultragarsas, vol. 62, No. 4, pp. 16-21.*
Svilainis et al., Optimization of the Ultrasonic Excitation Stage, Jun. 23-26, 2008, Proceedings of the ITI 2008 30th International Conference on Information Technology Interfaces, Cavtat, Croatia, pp. 791-796.*

* cited by examiner

*Primary Examiner* — Toan Le
(74) *Attorney, Agent, or Firm* — C. Tricia Liu

(57) ABSTRACT

Disclosed is a method and a phased array inspection device enabling calibration of the device with an optimized pulse rate, the pulse rate is derived based on the true adaptive value of the impedance of the specific phased array probe circuit or the pulser circuit and the circuit energy consumption limitations. The energy consumption limitations include the total energy made available by the power supply to the pulser and probe circuit and the pulser energy consumption with limitation due to pulser circuit's physical limit such as thermal limitation.

19 Claims, 9 Drawing Sheets

Table-1, Finding relationships between Transducer Impedance Ztransducer and pulser equivalent impedance Zeq using SPICE modeling results.
Assumptions: V = 115 v, pulse width = 50 ns

| Ztransducer (ohms) (assumed) | | 50 | 100 | 200 | 400 |
|---|---|---|---|---|---|
| Ptransducer (mW) (SPICE modeling) | transducer (20) | 162 | 99.3 | 55.4 | 29.4 |
| Ppulser (mW) (SPICE modeling) | Res_1 (18) | 35.3 | 12 | 4.46 | 2.32 |
| | Res_2 (13) | 78.5 | 79 | 79.5 | 80.7 |
| | Res_3 (12) | 21.3 | 21.3 | 21.3 | 21.3 |
| | mosfet (14) | 28.6 | 24.4 | 22.5 | 21.6 |
| | diode_1 (16) | 10 | 6.8 | 5.1 | 4.4 |
| | diode 2 (17) | 1 | 1 | 1 | 1 |
| | Res_ 4(19) | 4.25 | 6 | 7.5 | 8.5 |
| Ptotal (mW) (according to Eq. 2) | Ptotal (mW) | 340.95 | 249.8 | 196.76 | 169.22 |
| Zeq (Ohms) (according to Eq. 3) | Zeq (Ohms) | 38.78867869 | 52.94235388 | 67.21386461 | 78.15270063 |

Fig. 2a

Table-2, Finding relationships between Transducer impedance Ztransducer and pulser equivalent impedance Zeq using SPICE modeling results.
Assumptions: V = 115 v, pulse width = 100 ns

| Ztransducer (ohms) | | 50 | 100 | 200 | 400 |
|---|---|---|---|---|---|
| Ptransducer (mW) | transducer (20) | 162 | 99.3 | 55.4 | 29.4 |
| Ppulser (mW) | Res_1 (18) | 35.3 | 11.4 | 3.74 | 1.56 |
| | Res_2 (13) | 78.5 | 79 | 79.5 | 80.7 |
| | Res_3 (12) | 21.3 | 21.3 | 21.3 | 21.3 |
| | mosfet (14) | 13.3 | 13 | 13.7 | 13.3 |
| | diode_1 (16) | 9.6 | 6 | 4.4 | 3.6 |
| | diode 2 (17) | 1 | 1 | 1 | 1 |
| | Res_ (19) | 2.2 | 3 | 3.8 | 4.3 |
| Ptotal (mW) | Ptotal (mW) | 323.2 | 234 | 182.84 | 155.16 |
| Zeq (Ohms) | Zeq (Ohms) | 40.91893564 | 56.51709402 | 72.33099978 | 85.23459655 |

Fig. 2b

Table-3, Finding relationships between Transducer impedance Ztransducer and pulser equivalent impedance Zeq using SPICE modeling results.
Assumptions: V = 115 v, pulse width = 200 ns

| Ztransducer (ohms) | | 50 | 100 | 200 | 400 |
|---|---|---|---|---|---|
| Ptransducer (mW) | transducer (20) | 162 | 99.3 | 55.4 | 29.4 |
| Ppulser (mW) | Res_1 (18) | 35 | 11.1 | 3.37 | 1.18 |
| | Res_2 (13) | 78.5 | 79 | 79.5 | 80.7 |
| | Res_3 (12) | 21.3 | 21.3 | 21.3 | 21.3 |
| | mosfet (14) | 8.75 | 7 | 6.13 | 5.74 |
| | diode_1 (16) | 9.24 | 5.68 | 3.92 | 3.1 |
| | diode 2 (17) | 1 | 1 | 1 | 1 |
| | Res_ (19) | 1.11 | 1.55 | 1.92 | 2.18 |
| Ptotal (mW) | Ptotal (mW) | 316.9 | 225.93 | 172.54 | 144.6 |
| Zeq (Ohms) | Zeq (Ohms) | 41.7324077 | 58.53582968 | 76.64889301 | 91.45919779 |

Fig. 2c

Table-4, Finding relationships between Transducer impedance Ztransducer and pulser equivalent impedance Zeq using SPICE modeling results.
Assumptions: V = 115 v, pulse width = 500 ns

| Ztransducer (ohms) | | 50 | 100 | 200 | 400 |
|---|---|---|---|---|---|
| Ptransducer (mW) | transducer (20) | 162 | 99.3 | 55.4 | 28.9 |
| Ppulser (mW) | Res_1 (18) | 34 | 10.7 | 3.12 | 0.94 |
| | Res_2 (13) | 78.5 | 79 | 79.5 | 80.7 |
| | Res_3 (12) | 21.3 | 21.3 | 21.3 | 21.3 |
| | mosfet (14) | 5 | 3.97 | 3.27 | 3 |
| | diode_1 (16) | 8.87 | 5.4 | 3.6 | 2.8 |
| | diode 2 (17) | 1 | 1 | 1 | 1 |
| | Res_ (19) | 0.48 | 0.66 | 0.8 | 0.9 |
| Ptotal (mW) | Ptotal (mW) | 311.15 | 221.33 | 167.99 | 139.54 |
| Zeq(Ohms) | Zeq (Ohms) | 42.50361562 | 59.75240591 | 78.7249241 | 94.77569156 |

Fig. 2d

| Pulse width | K1 | K2 |
|---|---|---|
| 50n | 22.128 | -46.978 |
| 100n | 24.364 | -54.291 |
| 200n | 25.613 | -58.42 |
| 500n | 26.428 | -61.128 |

# METHOD AND A DEVICE OF PHASED ARRAY INSPECTION WITH PULSE RATE OPTIMIZATION

FIELD OF THE INVENTION

The present invention relates to non-destructive testing and inspection devices (NDT/NDI) and more particularly to a method of optimizing the pulse rate of a phased array ultrasonic inspection system.

BACKGROUND OF THE INVENTION

Phased array (hereafter PA) ultrasonic instruments have been used in non-destructive testing and instrument (NDT/NDI) applications to perform ultrasonic tests that include weld inspection, bond testing, thickness profiling, in-service crack detection, etc. Phased array probes typically comprise a transducer assembly with from 16 to as many as 256 small individual piezoelectric elements that can each be pulsed separately. Pulse rate, commonly known as pulse repetition frequency, is the rate at which an electrical pulse is applied to a piezoelectric element producing an ultrasound through a testing material. A pulser circuitry is usually employed to perform the pulsing tasks to energize each PA probe's element. A typical pulser circuitry of a phased array inspection system is shown in FIG. 1.

As can be seen in FIG. 1, the typical pulser circuitry mainly comprises two groups of components. The first group comprises a transducer or probe 20, the other portion embodies the whole pulser 10, which further includes electronics such as resistors 12, mosfet 14, diodes 16, analog switches 18, etc.

Ideally, in order to detect flaws with high resolution and high scanning efficiency, a phased array inspection system is setup with a pulse rate as high as possible. One prominent factor limiting the level of pulse rate is the maximum power consumption of the pulser circuit.

The amount of power that is transferred from the ultrasonic pulser circuit to a transducer is affected by the respective electronic components that comprise the pulser itself and by the impedance of the transducer. The transducer impedance magnitude, on the other hand, is affected by the excitation frequency (pulse width) of the pulser and the specific transducer coupled with the PA system and could change during the life of the specific transducer. The 'real' transducer impedance, or herein called "adaptive impedance" is therefore probe-specific and operational-setup-specific. Since the adaptive impedance of a transducer is not always readily known, in existing practice, assumed or fixed (static) transducer impedance is often arbitrarily given according to a worst case scenario to limit the maximum pulse rate specification of an instrument.

This limitation of the maximum pulse rate based on the assumed or static transducer impedance often means the phased array system is not set up in a way to provide the optimized pulsed rate. In typical industrial NDT applications where high pulse rate and high voltage is required, the maximum pulse rate specification could be increased up to 100% if the adaptive impedance of the transducer is known. However, existing practice has often seen to use 50 Ohms as fixed worst case transducer impedance. The problem associated with this existing practice is that it limits the performance and efficiency (scan rate and pulse rate) because typical transducer has greater impedance.

As can be seen that one critical factor leading to more accurately and dynamically gauging and optimizing the pulse rate is the capability to accurately measure the real, adaptive transducer impedance according to the probe and PA system setup. More specifically, with the adaptive transducer impedance more closely estimated, the amount of power that is transferred to the transducer versus the amount of power that remain within the pulser at any pulsing cycle is known and the pulse rate can be more accurately established.

Existing efforts addressing the measurement of transducer impedance has been seen in some industrial publications. One is presented by "Measurement of Complex Impedance of Ultrasonic Transducers", by L. Svilainis and V. Dumbrava. (later as "Svilainis and Dumbrava"). Svilainis and Dumbrava explains a way to measure the complex impedance of ultrasonic transducers with an approach to null out the reactive impedance (imaginary part of the complex impedance) to improve the performance of the transducer. However, for the case of solving the problem herein addressed, which is to maximize the phased array pulse rate, measuring the complex impedance is not of the concern of the present disclosure. What needs to be accurately measured is the resistance (magnitude) impedance, which is the real component of the complex impedance dealt by Svilainis and Dumbrava.

Another publication also by Svilainis and Dumbrava titled "Evaluation of the Ultrasonic Transducer Electrical Matching Performance" is published under ISSN 1392-2114 ULTRAGARSAS (ULTRASOUND), Vol. 62, No. 4, 2007 (later as Svilainis and Dumbrava II). The publication discusses how the performance of the transducer could be improved by adjusting the impedance of the generator. However, the solution taught in this publication does not apply to our pulsing technology, which is unipolar pulser. It applies to pulser using sine wave generator for Svilainis and Dumbrava II.

In addition, Svilainis and Dumbrava II do not deal with or include transducer impedance in their solution.

Another aspect of the background of the present disclosure is the usage of a widely known SPICE electronics simulation tool. A particular usage of the tool for ultrasonic device is mentioned in "SPICE SIMULATION OF TRANSIENT RESPONSES OF TRANSDUCERS AND SPIKE GENERATORS INCLUDED IN E/R ULTRASONIC SYSTEMS", published online on Digital CSIC by Ruiz Toledo A.; Ramos A.; San Emeterio, J. L.; Sanz Sanchez P. T., which is herein collectively referred as "SPICE". However, there is no effort seen in using SPICE to seek optimum pulse rate with given energy limit for phased array probes.

Thus, given that the existing practice uses less-than-optimum pulse rate and the existing efforts that do not address the issue effectively, solution providing optimized pulse rate is needed to improve the inspection efficiency.

SUMMARY OF THE INVENTION

The invention disclosed herein enables the optimization of pulse rate of phased array NDT/NDI devices, and therefore allow the increase of inspection accuracy and efficiency, whereas existing practice lacks an efficient approach to operate phased array systems at optimized pulse rate.

It should be noted that the terms "probe", "transducer", and "sensor" used herein may be used interchangeably. The terms "device", "instrument" and "system" all denote to the phased array NDT/NDI inspection assembly related to the present disclosure, and are used interchangeably.

It should also be noted that, "adaptive transducer impedance" or "true transducer impedance" disclosed and used in the present disclosure denotes to transducer impedance that is probe-specific and operation-setup-specific. Once the adaptive transducer impedance is calibrated for a specific probe and operation setup according to the present disclosure, it does not change during inspections. It is in contrast to the "assumed impedance" or "static impedance" which is used by existing previous practice as a fixed value without considering the specific probe or operational condition. Similarly, adaptive pulser equivalent impedance is also used in contrast with its static or assumed counterpart. All "transducer impedance" and "pulser impedance" by default denote to their adaptive forms in the present disclosure, unless "assumed" or "static" is noted.

Accordingly, it is a general objective of the present disclosure to enable the optimization of pulse rate of phased array NDT/NDI devices, and therefore allow the increase of inspection accuracy and efficiency.

Accordingly, it is a general object of the present disclosure to provide a method and an NDT/NDI instrument with the capability of gauging the magnitude portion of the adaptive impedance of phased array transducers, based on which to provide the fastest allowed scan rate for the phased array operation.

It is further an objective of the present disclosure to provide a method to determine the adaptive impedance of transducer(s) and thus deduced the amount of energy consumed by pulser circuit versus the energy effectively transferred into the transducer(s). The energy available for the transducer is an indication of how fast scan rate can be deployed for a specific PA instrument.

It is further an objective of the present disclosure to provide a method to make use of electronics simulation tool, such as PSPICE, and curve fitting to determine the intrinsic relationships between the transducer impedance and equivalent pulser impedance.

It is further an objective of the present disclosure to provide a method and a PA instrument to conduct on-site measurement of voltage and current at the pulse power supply and to deduce the true value of energy consumption of the transducer. With known relationship between the true transducer impedance and the total power consumption, PA can be pulsed at the highest possible rate and the PA system can be operated more efficiently.

It is yet another objective of the present disclosure to provide a method of using the true pulser impedance value to gauge the power consumption by the pulser circuit, and further using the pulser's electronics thermal limit to gauge the maximally allowed pulse rate.

Many advantages provided by the present disclosure include increasing the performance of the PA instrument by significantly increasing the pulse rate (scan rate) to its maximally allowed value, without increasing the size of the high voltage power supply.

It can be understood that the presently disclosed method and PA instrument provide the advantages of using highestly allowed scan rate and providing inspections with higher productivity.

BRIEF DESCRIPTION OF THE DRAWING(S)

FIG. 1 is a prior art schematic diagram showing a typical PA pulser circuitry, to which the presently disclosed pulse rate optimization method can be applied.

FIGS. 2a, 2b, 2c and 2d are exhibitions of tables presenting the data points generated from SPICE model for the pulser circuit 10; the data points are employed by the method according to the present disclosure to establish relationships between transducer impedance and pulser equivalent impedance when pulse width is set at 50 ns, 100 ns, 200 ns and 500 ns, respectively.

Figure 7:
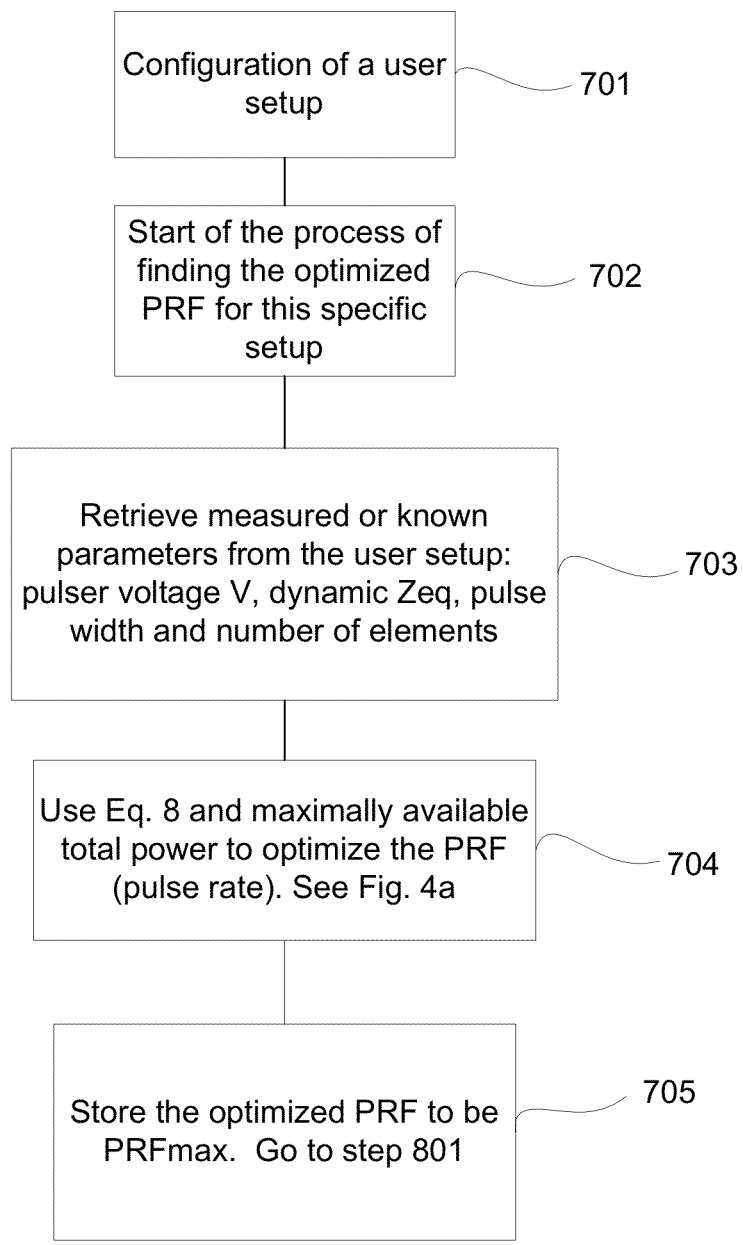

FIG. 7 describes the Total Energy Pulse-rate Optimizer showing flow chart of the steps of seeking optimized pulse rate, with the true transducer impedance known, meeting total power consumption requirement.

Figure 8:
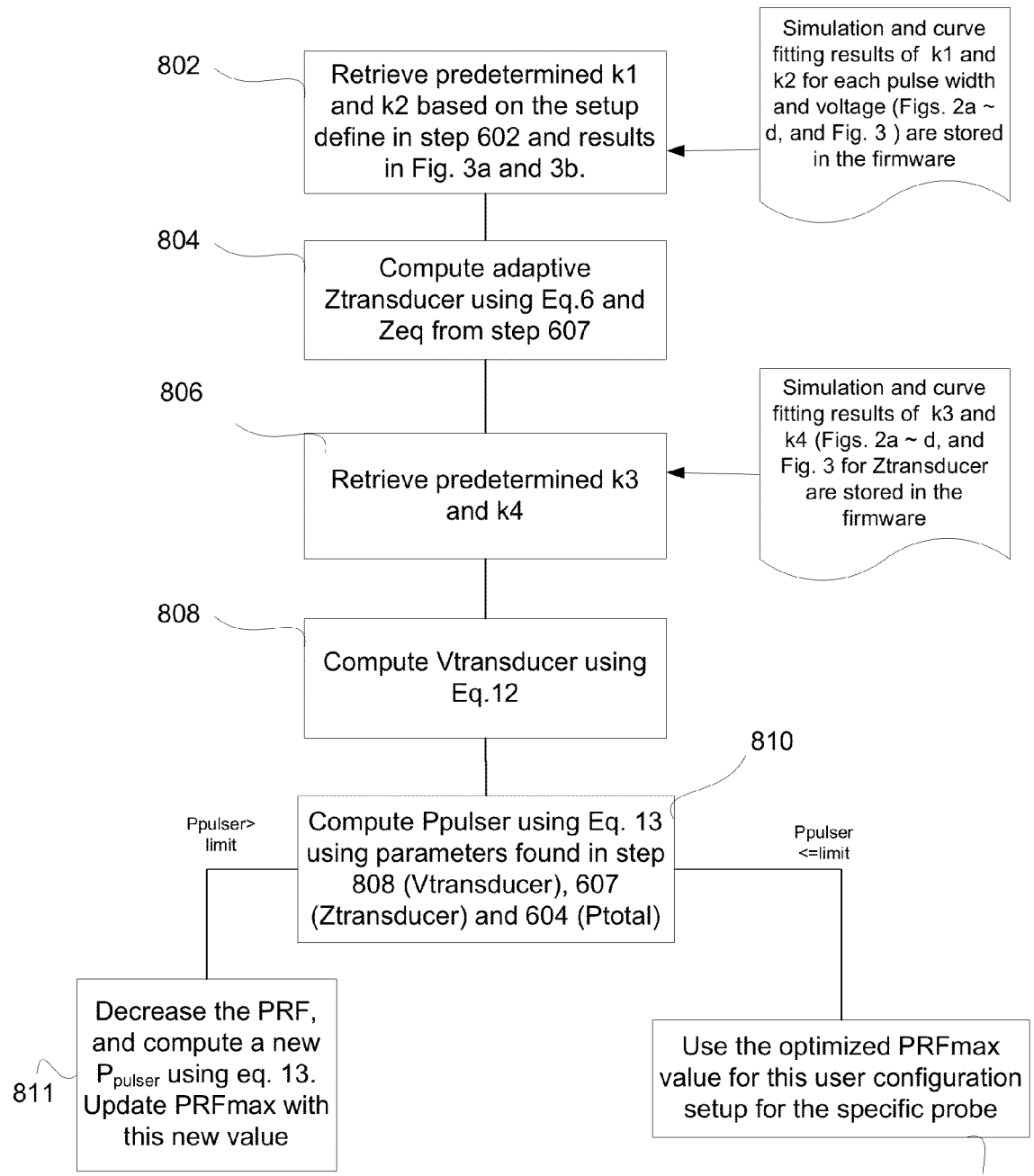

FIG. 8 delineates the Thermal Energy Pulse-rate Optimizer, showing the steps of seeking optimized pulse rate, with the true transducer impedance known, meeting both total power consumption requirement and the pulser thermal (power consumption) limit.

DETAILED DESCRIPTION OF PREFERRED EMBODIMENT

Figure 1:
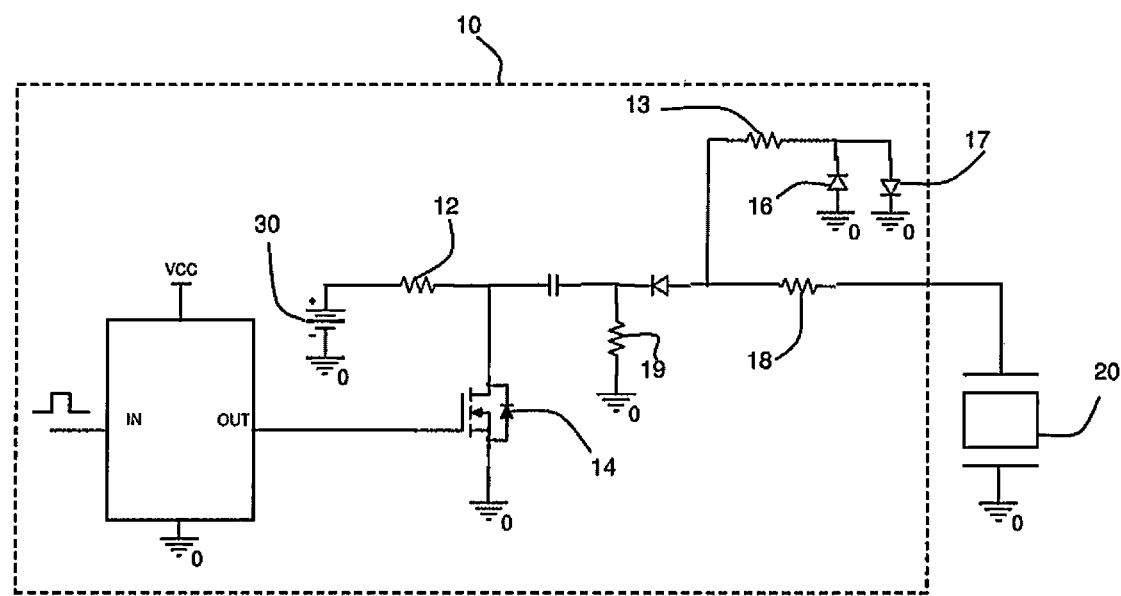

FIG. 1 illustrates a conventional prior art circuitry for a typical circuitry for phased array probe pulser 10. As can be seen in FIG. 1, the conventional pulser-probe circuitry can be grouped into two portions, one comprises a transducer or probe 20, the other portion embodies the whole pulser 10, which further includes electronics such as resistors 12, mosfet 14, diodes 16, analog switches 18, etc. This typical pulser circuitry is also used as an exemplary pulser circuitry by the present disclosure.

One of the principles that the presently disclosed method is based on is the understanding that when a high power voltage is given at power supply 30, the electric power $P_{total}$ produced by this power supply is transmitted and distributed among pulser circuit 10 with $P_{pulser}$ and transducer circuit 20, with, $P_{transducers}$, which yields:

$$P_{total} = P_{pulser} + P_{transducers} \qquad \text{Eq. 1}$$

It can be seen from FIG. 1 that $P_{pulser}$ is the summation of the power lost within all discrete pulser elements, such as resistors 12, mosfet 14, diodes 16, analog switches 18, etc.

Another principal involves the basic understanding that once a pulser circuitry, such as 10 and transducer circuit 20 are designed; there is an intrinsic physical limit to the total power consumption $P_{total}$. It is widely known that, in general, higher the pulse-rate, higher the total power consumption. It is however, one of the objectives of the present disclosure to determine and quantify the relationship between the pulse rate and the total power consumption, with the true adaptive pulser impedance found using the method later described in this disclosure.

Yet another aspect of the present disclosure is to examine the limit of the pulser power consumption imposed by the thermal limit of the pulser. It is widely known that any electronic circuitry has thermal limit and its corresponding limit to power consumption of the circuit. The power consumption of the pulser with the transducer impedance specific to the probe and pulser adaptive conditions (herein after referred to as "adaptive transducer impedance) is deduced and separated from the total power consumption. The pulser power consumption is calculated based on true measurement of the adaptive conditions including the adaptive value of the transducer impedance. The thermal limit on the pulser power consumption is then imposed on the pulse rate, which is another aspect of seeking optimization of the pulse rate.

It is then conceivable that the optimized pulse rate is the highest pulse rate that meets the limit of total power consumption by both pulser and transducer, and the pulser power consumption with a limit imposed by the thermal limit of the pulser circuit.

Using SPICE Model and Curve Fitting to Determine the Relationship Between Pulser Impedance and the Transducer Impedance For a given phased array NDT instrument, all the discrete elements found on a pulser circuit such as that of 10 are already known. Power consumption of each discrete element varies depending on various factors including voltage at power supply 30, pulse width according to the setup of the phased array operation and the adaptive or operational value of transducer impedance. It is also known that one can use SPICE modeling to deduce the power consumption for all the discrete elements of the known pulser circuits. One novel aspect of the present disclosure is to provide a method to establish relationship (mathematical equations) between the power consumption lost inside pulser circuit 10 and the various factors affecting the power consumption, and subsequently finding the pulser power consumption using Eq. 1.

To deduce those equations governing pulser circuit power consumption and other pulser parameters, such as pulse rate and transducer impedance, a SPICE model on circuit 10 shown in FIG. 1 is established. As mentioned in the BACKGROUND OF THE INVENTION of the present disclosure, SPICE is herein employed and its method is used to construct equations that model the power dissipation on all components in relation to various parameters such as voltage/pulse width/ transducer impedance. As mentioned before that SPICE is widely known and used for electronics simulation and modeling.

Once the SPICE model is build, the power of each component is computed by the SPICE simulator. For modeling purpose, an array of parameters are varied with a series of assumed values such as those for voltage, pulse width and transducer impedance. Tables exhibited in FIGS. 2a, 2b, 2c and 2d show an example of the data extracted from the SPICE simulation.

As can be seen in FIGS. 2a, 2b, 2c and 2d, power consumption of each circuit component of pulser 10 is simulated under the conditions when pulser voltage at power supply 30 is set to be 115 v and the pulse width set to be 50 ns, 100 ns, 200 ns and 500 ns, respectively.

Referring to FIG. 2a, using Table-1 for example, it can be seen that, the total power consumption in each pulsing cycle is, $$P_{total} = P_{Res\_1} + P_{Res\_2} + P_{mosfet} + P_{diode\_1} + P_{diod\_2} + P_{Res\_4} + P_{Transducer} \qquad \text{Eq. 2}$$

wherein, the power consumption of each element on the right-hand side of Eq. 2 is resulted from SPICE model simulation of pulser circuitry shown in FIG. 1, more particularly, $P_{Res\_1}$, $P_{Res\_2}$, $P_{Res\_3}$, $P_{Res\_4}$ are the power consumptions of resistors 18, 13, 12 and 19, respectively;

$P_{mosfet}$ is the power consumption of mosfet 14;

$P_{diode\_1}$ and $P_{diode\_2}$ are the power consumptions of diodes 16 and 17, respectively.

In an exemplary case as shown in column 3 in FIG. 2a, with pulse width being set to be 50 ns and transducer impedance assumed to be 50Ω, the power consumption of each component is simulated with result being listed. For example, the simulation result for transducer power consumption ($P_{transducer}$) is 162 mW. The simulation result for resistor 1 (18) power consumption is 35.3 mW. Using the result of $P_{total}$ calculated by the Eq. 2, as shown in Table-1 of FIG. 2a, more specifically as shown in column three of Table 1, the equivalent impedance of the pulser 10 and transducer 20 under with power supply voltage 115V and pulse width of 50 ns can be calculated according to following Eq. 3, $$Z_{eq} = \frac{V^2}{P_{total}} \qquad \text{Eq. 3}$$

where V is the voltage at the power supply 30, which is 115 Volt, known and given to the SPICE model in this example;

$Z_{eq}$ is the equivalent impedance of pulser circuit 10 and the transducer circuit 20.

Continuing with FIG. 2a, similar simulation and calculation can be performed for conditions when the transducer impedance is assumed to be 100, 200 and 400 ohms, respectively. Now we have equivalent pulser impedance deduced for four different values of transducers impedance in a simulation while the pulser voltage is 115V and the pulse width is 50 ns as shown in Table-1. See resulted $Z_{eq}$ in columns D, E and F calculated using Eq. 3 and listed in Table-1 of FIG. 2a. As a result of calculation shown in FIG. 2a, four pairs of values of transducer impedance $Z_{transducer}$ and pulser equivalent impedance $Z_{eq}$ are found and ready to be used in later steps of building relationship between $Z_{transducer}$ and $Z_{eq}$.

It should be noted from the above operation that one novel aspect of the present disclosure is that transducer impedance $Z_{transducer}$ is unknown, but are assumed as constant 50, 100, 200 and 400 ohms in the interpolation process of defining relationship between transducer impedance $Z_{transducer}$ and equivalent pulser impedance $Z_{eq}$.

Reference is now turned to FIGS. 2b, 2c and 2d, in which power supply voltage are all assumed to be 115 V and the pulse width are assumed to be 100 ns, 200 ns and 500 ns, respectively. Power consumptions of different discrete components are simulated by SPICE model. The total power consumption under each situation is calculated using Eq. 2. Then equivalent impedance of pulser 10 and transducer 20 is calculated using Eq. 3 under each situation. Subsequently, similar to the exhibition shown in FIG. 2a, for each table shown in FIGS. 2b, 2c and 2d, four pairs of $Z_{transducer}$ and $Z_{eq}$ are found and the values of which are ready to be used to establish relationship between $Z_{transducer}$ and $Z_{eq}$.

Figures 3A, 3B:
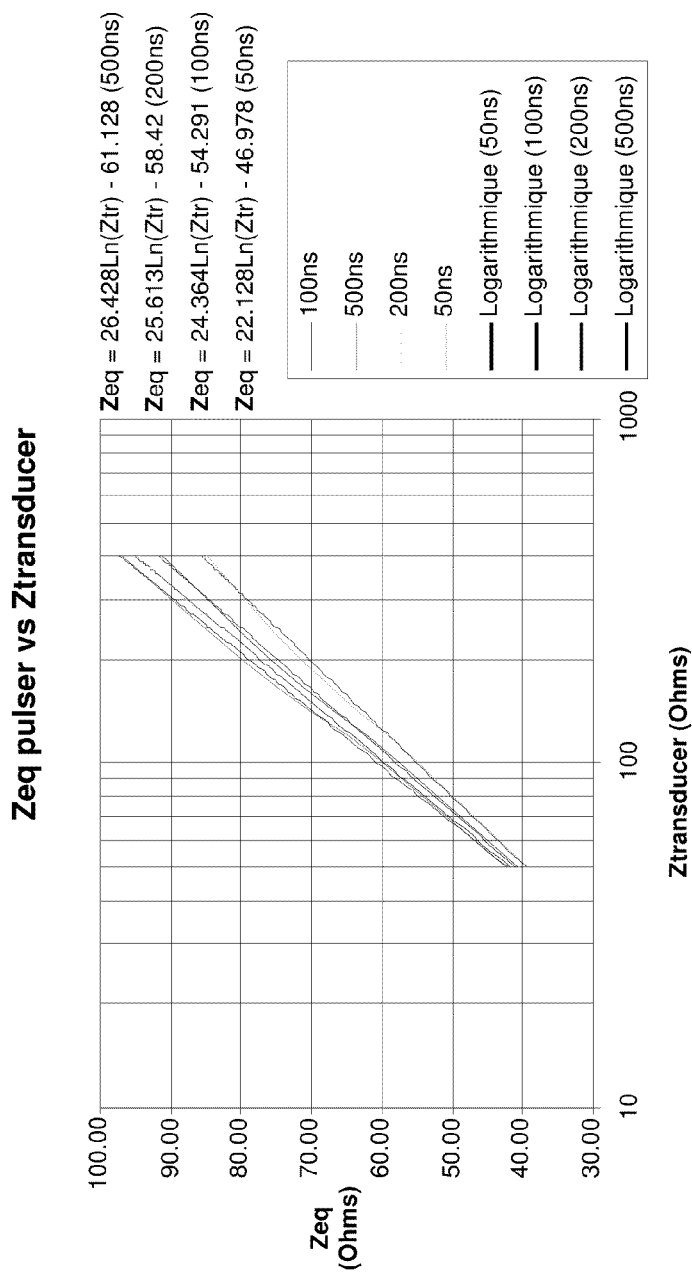
FIGS. 3a and 3b are exhibitions showing the curve fitting process according to the presently disclosed method, to establish relationships between transducer impedance and pulser equivalent impedance when pulse width is set at 50 ns, 100 ns, 200 ns and 500 ns, respectively.

Reference is now made to FIG. 3a, which shows a curve fitting process establishing the relationship between $Z_{transducer}$ and $Z_{eq}$ for each specific phased array probe.

Graphics shown in FIG. 3a are four lines which are simple representation of the data obtained in the above simulation process with pairs of values for $Z_{transducer}$ and $Z_{eq}$ as exhibited in Tables 1~4 in FIGS. 2a-2d for assumed pulse width of 50 ns, 100 ns, 200 ns and 500 ns, respectively.

Curve fitting methods, such as Logarithmic curve fitting known to those skilled in the art can be used to extract one equation for each group of data points for $Z_{transducer}$ and $Z_{eq}$ for each pulse width as follows.

$$Z_{eq} = k_1 \ln(Z_{transducer}) - k_2 \qquad \text{Eq. 4}$$

It should be appreciated that any other curve fitting method known in the art can be employed to extract the equation for each group of data points for $Z_{transducer}$ and $Z_{eq}$, which is within the scope of the present disclosure.

As shown in FIG. 3a, as well as FIG. 3b, for each transducer pulse width, a pair of $k_1$ and $k_2$ value is deduced from the curve fitting process. For example, a specific equation between $Z_{transducer}$ and $Z_{eq}$ for pulse width 50 ns is, $$Z_{eq} = 22.128 \ln(Z_{transducer}) - 46.978 \quad \text{Eq. 5 for pulse width=50 ns}$$

It should be understood that method of interpolation known to those skilled in engineering can be used for transducer pulse width values that falls between any two values herein presented. Corresponding function for $Z_{eq}$ and $Z_{transducer}$ can therefore be established in similar method using the interpolated data.

One can now deduce based on Eq. 4 that, $$Z_{transducer} = e^{\frac{Z_{eq}+K_2}{K_1}} \quad \text{Eq. 6}$$

Referring to FIGS. 3a and 3b, again using the exemplary case of 50 n pulse width, $$Z_{transducer} = e^{\frac{Z_{eq}-46.978}{22.128}} \quad \text{Eq. 7}$$

The above relationship establish in Eqs. 5~7 through SPICE modeling of the circuit and curve fitting will be later used in finding the optimized pulse rate in the further description provided below.

Measurement and Deriving the True Adaptive Transducer Impedance

It should be again noted that in the preceding description of the preferred embodiment, transducer impedance are unknown but assumed constant (row one of Tables 1-4 in FIGS. 2a~2d), in order to establish relationship between $Z_{eq}$ and $Z_{transducer}$. Next, with measurement of parameters during a PA operation, such as power supply voltage V and current I at power supply 30 (FIG. 1), total power consumption can be obtained dynamically and the adaptive values of $Z_{eq}$ and $Z_{transducer}$ can be further determined from these measurements.

Once the power consumption consumed within pulser circuit 10 under any operation condition is known, the instant power consumption of transducer 20 can be dynamically deduced, which provides the basis to optimize the pulser pulse rate.

There are many ways of measuring the power $P_{total}$ provided by the high voltage power supply. The preferred embodiment includes the steps of constantly monitoring the output voltage V and the output current I at outflow at power supply 30.

Note that for a phase array instrument with multiple pulsers, the total power consumption in watt is defined by, $$P_{TotalinWatt} = V*I*DutyCycle*N_{ch} \quad \text{Eq. 8}$$

wherein,
DutyCycle=PulseWidth*PulseRate;
Nch is the number of active pulsers;
V is the voltage measured at power supply 30;
I is the current measured at power supply 30.

It should be noted that $P_{Total\ in\ Watt}$ is the total power consumption expressed in Watt. $P_{Total}$ in Equ. 1 then equals to $P_{Total\ in\ Watt}$ when $N_{ch}$ is equal to one.

Now recalling in Eq. 3, Eq. 7 and referring back to FIG. 1, with measured voltage at power supply V and total power consumption $P_{total}$, we could compute $Z_{transducer}$.

$$Z_{transducer} = e^{\frac{\frac{V^2}{P_{total}}+K_2}{K_1}} \quad \text{Eq. 9}$$

Therefore the adaptive value of the transducer impedance is derived based on measurement of the specific pulser circuit.

Optimization of Pulse Rate Based on the Limit of Maximally Available Power

Getting back to the goal of the present disclosure seeking optimization of pulse rate and now with adaptive transducer impedance being measured for a specific probe and pulser setup, the task is moved onto providing guiding relationship between the power consumption and the pulse rate with established adaptive impedance for the given probe.

As mentioned before, one prominent factor limiting the level of pulse rate is the maximum total power consumption of the entire pulser and transmitter circuit. With now the true value of transducer impedance $Z_{transducer}$ found, the relationship between the high voltage circuit estimate power consumption $P_{total}$ and $Z_{eq}$ is given as another form of Eq. 8 as, $$P_{total} = \frac{V^2}{Z_{eq}} * PulseWidth * PRF * N_{ch} \quad \text{Eq. 10}$$

Figure 4A:
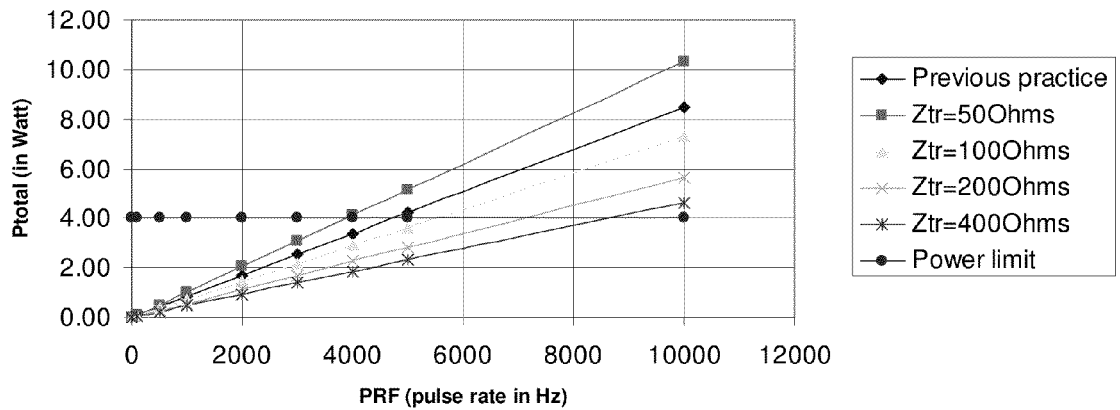
FIG. 4a is a chart showing the plotted relationship between total power consumption and pulse rate, with adaptive transducer impedance for each exemplary probe and operation-setup and with assumed transducer impedance as in previous practice.

Reference now is turned to FIG. 4a, which depicts the process of finding the maximally allowed pulse rate (PRF) based on the limitation of total power consumption. As can been seen, according to the above Eq. 10, the relationships between total power consumption $P_{total}$ and respective pulse rate (PRF) are plotted for measured (adaptive) values of transducer impedance ($Z_{tr}$) for a few different probes, for 50 ohms, 100 hms, 200 ohms and 400 ohms, respectively.

The difference is shown between the curves for the probes with each with respective adaptive transducer impedance obtained based on specific probe circuit and measurement and the curve with the transducer impedance being assumed (diamond legend). With known limitation for available total power supply available, being 4 Watts in this case, the maximally allowed PRF for the assumed transducer impedance is about 4800 Hz using the previous practice. However, for values of adaptive transducer impedance for different probes, the values of optimal pulse rate range between 4000 and 8800 in Hz. This shows a clear advantage of using the presently disclosed method to determine the optimal pulse rate.

Finding the Maximum Pulse Rate Due to Thermal Limit of the Pulser Energy Consumption Effectively, for most of instruments, there is a restricted limit for operating temperature in order for electronic components to work properly. It is understandable that power consumed inside the pulser circuit results in elevation of internal temperature and eventually causes the internal temperature to reach its functional limit.

Therefore, besides the total power available for pulser and transducer, it can be appreciated that pulse rate PRF is also limited by the power consumption within the pulser circuit. The relationship between pulse-rate PRF and the pulser power consumption based on adaptive transducer impedance is developed in the following.

As it is known to those skilled in the art, $$P_{transducer} = \frac{V_{transducer}^2}{Z_{transducer}} \quad \text{Eq. 11}$$

wherein $V_{transducer}$ is the voltage measured between pulser circuit 10 and transducer 20 in FIG. 1.

$Z_{transducer}$ is the transducer impedance, the same as defined in previous discussions.

Referring back to FIGS. 2a, 2b, 2c and 2d, and using the same SPICE model and the curve fitting method described in above in association with FIGS. 2a, 2b, 2c and 2d and FIG. 3, a relationship between $V_{transducer}$ and $Z_{transducer}$ can be establish in the format of:

$$V_{transducer} = k_3 \ln(Z_{transducer}) - k_4 \quad \text{Eq. 12}$$

With adaptive value established for $Z_{transducer}$ according to circuitry measurement and Eq. 10, and combining Eq. 1 and Eq. 12, one can now find the relationship between pulse rate and the power consumption of pulser circuit as:

$$P_{pulser} = P_{total} - P_{transducer} \quad \text{Eq. 13}$$

or $$P_{pulser} = \left(\frac{V^2}{Z_{eq}} - \frac{V_{transducer}^2}{Z_{transducer}}\right) * PulseWidth * PRF * N_{ch} \quad \text{Eq. 14}$$

Figure 4B:
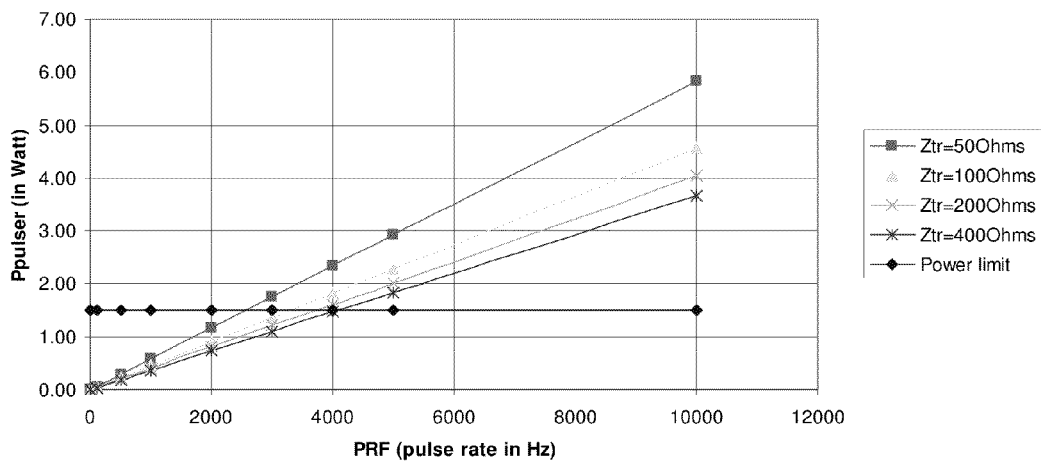
FIG. 4b is a chart showing the plotted relationship between the pulser power consumption and pulse rate with adaptive transducer impedance for each specific exemplary probe and operation-setup specific.

Reference is now turned to FIG. 4b. Similar to the method described above related to FIG. 4a for finding maximum pulse rate according to total power consumption limit, as seen in FIG. 4b, the relationship between the pulser power consumption $P_{pulser}$ and the pulse rate (PRF) is plotted according to Eq. 14 for the adaptive transducer impedance for 50 ohms, 100 ohms, 200 ohms and 400 ohms, respectively. With an exemplary known thermal limitation restricting pulser power consumption on a predetermined setup being, 1.5 Watts, the maximally allowed PRF are 2500, 3300, 3800 and 4100, respective, all in Hz.

The optimum pulse-rate is then established to be the lesser value of PRFs determined in FIGS. 4a and 4b, specifically for each probe. For the exemplary case for the probe with adaptive transducer impedance of 100 ohms (triangle legend), the maximally allowed PRF is 5200 Hz according to FIG. 4a for total power available; the maximally allowed PRF is about 3300 Hz according to FIG. 4b due to thermal limitation. Therefore the maximally allowed pulse rate (PRF) for this particular probe and for power supply V=115 v and PA setup with pulse width=100 ns is 3300 Hz.

Calibration Steps and Software Modules

Figure 5:
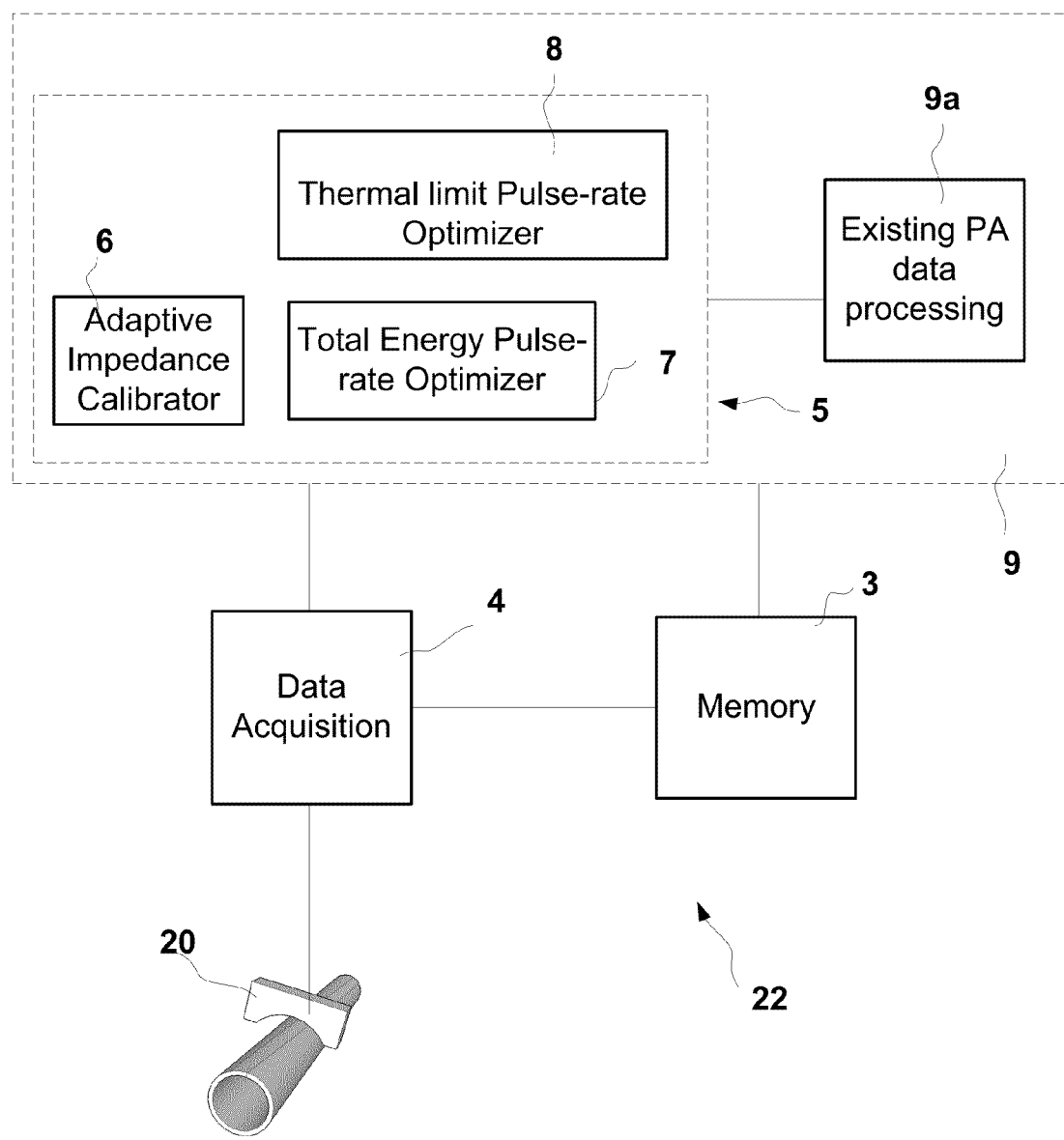
FIG. 5 is a schematic view of the preferred embodiment including elements providing pulse rate optimization for the PA system.

Reference is now made to FIG. 5. The method as described above to calibrate the phased array system with the optimized pulse-rate is preferably implemented by a preferred embodiment embodying a phased array instrument 22 comprising one or more software modules which are executable by any PA digital processing circuits. Instrument 22 includes the elements that are included in an existing conventional PA instrument 22a (not encircled), which typically includes a memory 3, a data acquisition unit 4 and a data processor 9a. The presently disclosed preferred embodiment further embodies a pulse rate optimizer 5 which is added to existing processor 9a and form digital processor 9 for the preferred embodiment. Optimizer 5 can be part of the digital processor 9 or to be couple or loaded onto the existing data processor 9a of an existing phased array inspection product. In another word, one of the advantages of the presently disclosed method is its easy implementation by simply adding modules of executable coding onto existing design or product of PA inspection. The software modules herein referred are collectively named as the "pulse-rate optimizer" 5. The pulse rate optimizer 5 includes an adaptive impedance calculator 6, a total energy consumption pulse rate optimizer 7 and a pulser energy consumption pulse rate optimizer 8 as shown in FIG. 5 and further detailed in FIGS. 6, 7 and 8 respectively. Pulse rate optimizer 8 is also called Thermal Limit Pulse-rate optimizer for the reasons provided in method description.

Figure 6:
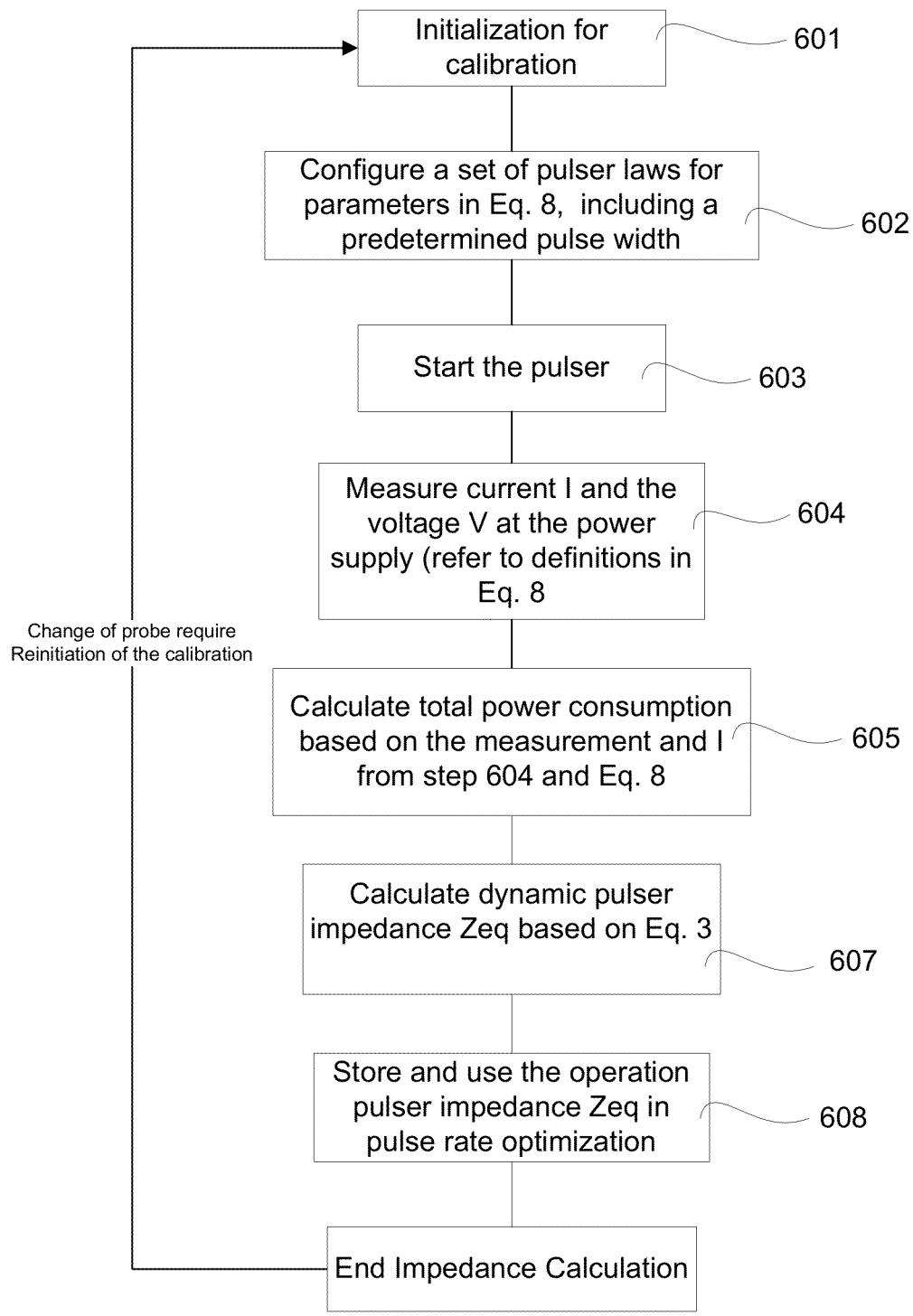
FIG. 6 is a flow chart block diagram showing the steps and sub-modules of the Adaptive Impedance Calculator.

FIG. 6 is a flowchart blocks depicting the sub-coding modules and/or steps embodying the adaptive impedance calculator 6, which is turned on each time when a new probe is changed and engaged with PA instrument 22.

It should be noted that for the subsequent description, the definitions for all the parameter symbols are kept the same as they are defined in the preceding method description. All the reference to equation numbers denote to equations provided in the preceding description as well.

As shown in FIG. 6, in step 601, the pulse-rate optimizer receives instruction that PA system 22 needs a pulser calibration session. In step 602, the adaptive impedance calculator records new configurations with a set of predetermined acquisition parameters. The acquisition parameters include those involved in Eq. 8, such as pulse width of the PA system. Nch is also included in the acquisition parameters, which is the number of transducer that is employed for the calibration and later inspection sessions.

Continuing with FIG. 6, in step 603, focal law is applied to test object via transducer (probe) 20 according to the configuration in step 602. In step 604, the following parameters from Eq. 8 are measured.

V, the measured voltage at power supply 30 in FIG. 1

I, the measure current at inflow of resistor 12 in FIG. 1

At step 605, total power consumption is calculated based on the measurement in step 604 and Eq. 8. At step 607, adaptive pulser impedance $Z_{eq}$ is computed according to Eq. 3 and stored in a configuration file for the current usage of the instrument in step 608. The configuration file, not shown, can be resided within a memory of system 22 or 22a.

Reference is now made to FIG. 7 depicting the sub-coding modules and/or steps embodying the total energy pulse-rate optimizer 7, which is turned on each time when the system is adjusted with a new setup, such as a new pulse-width.

In step 701, optimizer 7 records a changed in new user setup for operational parameters such as pulse width or voltage. In step 702, optimizer 7 starts the process of finding a new optimized pulse rate for the new setup parameters. In step 702, optimizer 7 retrieves all the parameters from the user setup for pulser voltage, pulse width and number of transducer elements and the calculated adaptive impedance from step 608. In step 704, the optimizer 7 uses Eq. 8 and the process demonstrated in FIG. 4a, and the given maximally available total power supply to find the optimized pulse rate $PRF_{max}$. The value for $PRF_{max}$ is stored in step 705.

Reference is now made to FIG. 8, depicting the sub-coding modules and/or steps embodying thermal limit or pulser energy pulse-rate optimizer (later short as Thermal Optimizer 8). Thermal Optimizer 8 is turned on each time when the system is adjusted with a new setup, such as a new pulse-width.

In step 802, thermal optimizer 8 records a changed in new user setup for operational parameters such as pulse width or voltage and retrieves predetermined k1 and k2 based obtained from SPICE model and curve fitting shown in FIG. 3. In step 804, thermal optimizer 8 computes adaptive $Z_{transducer}$ using Eq. 6 and $Z_{eq}$ from step 607. In step 806, thermal optimizer 8 retrieves predetermined k3 and k4 obtained from SPICE model and curve fitting in a process similar to the process shown in FIG. 3 and as explained in method description. In step 808, $V_{transducer}$ is computed according to Eq. 12. In step 810, the process calculates the power consumption by the pulser alone (not including consumption of the transducer) using Eq. 13 and parameter values obtained in steps 808 for $V_{transducer}$, 607 for $Z_{transducer}$. In step 810, thermal optimizer 8 determines if the pulser energy consumption has exceeded its thermal limit (given according to industry standard for electronic components for specific pulser circuit). If yes, Thermal Optimizer 8 decreases the $PRF_{max}$ and compute a new $P_{pulser}$ using Eq/13 and updates the new $PRF_{max}$. If not, in step 812, thermal optimizer uses the $PRF_{max}$ value obtained in step 705.

Although the present invention has been described in relation to particular exemplary embodiments thereof, many other variations and modifications and other uses will become apparent to those skilled in the art. It is preferred, therefore, that the present invention not be limited by the specific disclosure. For example, the scope of the present disclosure may be applied to a wide range of probes such as, but not limited to Ultrasonic (UT) single element, multi-element, and array probes and Eddy Current probes.

What is claimed is:

1. A phased array inspection device for inspecting target objects using a plurality of phased array probes, each of the probes is exchangeably engaged with the device and includes a respective probe circuitry, the device comprising:
    a pulser circuit configured to cause each of the probes to pulse ultrasonic energy into the objects,
    a data processor for data acquisition and processing and providing output of inspection result, the data processor further including a memory and a pulse repetition rate optimizer,
    wherein the pulse repetition rate optimizer is configured to acquire adaptive impedance of the respective probe circuitry and of the pulser circuit, based on which the optimizer further provides an optimized pulse repetition rate for the device to be operated for the respective probe.

2. The phased array inspection device of claim 1, wherein the pulse repetition rate optimizer further comprises an adaptive impedance calculator and an energy limit pulse repetition rate optimizer.

3. The phased array inspection device of claim 2, wherein the adaptive impedance calculator calculates either adaptive equivalent impedance of the pulser circuit or adaptive impedance of the respective probe based on measurement made on a predetermined operational set up of the device and the respective probe being engaged.

4. The phased array inspection device of claim 3, wherein the energy limit pulse repetition rate optimizer further comprises a total energy pulse repetition rate optimizer which is operable in conjunction with the adaptive impedance calculator.

5. The phased array inspection device of claim 4 wherein the pulse repetition rate optimizer calculates the optimized pulse repetition rate according to the total energy available from a power supply and the relationship between the total energy and the pulse repetition rate (PRF), which is:

$$P_{total} = \frac{V^2}{Z_{eq}} * PulseWidth * PRF * N_{ch}$$

wherein,
    PulseWidth is the pulse width given as part of the operational setup;
    Nch is the number of active elements of the respective pulser;
    V is the voltage measured at a power supply 30 of the pulser circuit;
    $Z_{eq}$ is the equivalent impedance of the pulser circuit.

6. The phased array inspection device of claim 4, wherein a relationship between the impedance of the pulser circuit and impedance of each of the respective probe circuitry is determined by employing electronics simulations and curve fitting, the relationship is stored in the memory.

7. The phased array inspection device of claim 6, wherein the pulser circuit including a plurality of electronic components which are pertaining to a number of electronic parameters representing at least one characteristics of the pulser circuit, and, the electronic simulations is conducted with the following parameters as input:
    a) series of assumed pulse width, each of which is given a series of assumed values of equivalent impedance of probes,
    b) the electronic parameters of all electronic components of the pulser circuit,
    c) the characteristics of the pulser circuit.

8. The phased array inspection device of claim 7, wherein the simulations provide the values of equivalent impedance of the pulser circuit when the pulser is assumed to be operating with the probes with a plurality of assumed values of probe impedance, each for a plurality of assumed values for pulse width, by such, a plurality pairs of values of equivalent impedance of the pulser circuit and the impedance of a respective probe are formed and provided for the curve fitting process.

9. The phased array inspection device of claim 8, wherein the relationship is characterized a first factor k1 and second factor k2 used in an equation, $$Z_{eq} = k_1 \ln(Z_{transducer}) - k_2$$

Where $Z_{eq}$ is the equivalent impedance of the pulser $Z_{transducer}$ is the equivalent impedance of probes.

10. The phased array inspection device of claim 9, wherein the energy limit pulse repetition rate optimizer further comprises a thermal limit pulse repetition rate optimizer which is operable in conjunction the adaptive impedance calculator, wherein the thermal limit denotes to the level of energy consumption allowed within the pulser circuit.

11. The phased array inspection device of claim 10, wherein the pulse repetition rate optimizer calculates the optimized pulse repetition rate according to the allowed power consumption within the pulser circuit and the relationship between the pulser circuit energy consumption and the pulse repetition rate (PRF), which is:

$$P_{pulser} = \left(\frac{V^2}{Z_{eq}} - \frac{V^2_{transducer}}{Z_{transducer}}\right) * PulseWidth * PRF * N_{ch}$$

wherein,
    PulseWidth is the pulse width given as part of the operational setup;

Nch is the number of active elements of the respective pulser;

V is the voltage measured at a power supply 30 of the pulser circuit, $V_{transducer}$ is the voltage measured between probe circuit and pulser circuit;

$Z_{eq}$ is the adaptive equivalent impedance of the pulser circuit, $Z_{transducer}$ is the adaptive impedance of the respective probe.

12. The phased array inspection device according to claim 11, wherein the optimized pulse repetition rate is the lesser of the optimized pulse repetition rate according to the total energy limit and the optimized pulse repetition rate according to the allowed power consumption within the pulser circuit.

13. A method of calibrating a phased array device for non-destructive inspection, the device is configured to be operable with a plurality of phased array probes, each of which includes a respective probe circuitry, wherein the device includes a pulser circuit configured to cause each of the probes to pulse ultrasonic focal laws and a data processing unit which further includes a memory, wherein the focal laws include a pulse repetition rate for the respective probe to be pulsed, the method comprising the steps of:
a) measuring and calculating adaptive impedance of the pulser circuit and the respective probe circuit,
b) determining the relationship between total energy and the pulse repetition rate, wherein the total energy is the energy available from a power supply for the pulser and the respective probe circuit, and the total energy is a function of the adaptive impedance,
c) deducing a first maximally allowed pulse repetition rate based on a known limit for the total energy,
d) determining the relationship between pulser energy consumption and the pulse repetition rate, wherein the pulser energy consumption is the energy consumed by the pulser circuit and is a function of the adaptive impedance,
e) deducing a second maximally allowed pulse repetition rate based on a known limit for the pulser energy consumption,
f) determining an optimized pulse repetition rate value by choosing the lesser value of the first and the second maximally allowed pulse repetition rate;
g) calibrating the device to be operated for the respective probe at the optimized pulse repetition rate.

14. The method of claim 13, wherein the adaptive impedance of the pulser circuit or the respective probe circuitry is obtained calculated on measurement made on the pulser and probe circuit with a predetermined operational set up of the device and the respective probe being engaged.

15. The method of claim 14, wherein a relationship between equivalent impedance of the pulser circuit and equivalent impedance of the each of the respective probe circuitry is determined by employing electronics simulations and curve fitting, the relationship is stored in the memory.

16. The method of claim 15, wherein the pulser circuit including a plurality of electronic components which are pertaining to a number of electronic parameters representing at least one characteristics of the pulser circuit, and, the electronic simulations is performed with the following parameters as input:
a) a series of assumed pulse width, each of which is given a series of assumed values of equivalent impedance of probes,
b) the electronic parameters of all electronic components of the pulser circuit,
c) the characteristics of the pulser circuit.

17. The method of claim 16, wherein the simulations provide the values of equivalent impedance of the pulser when the pulser is assumed to be operating at each assumed respective probe impedance for each respective pulse width, and the relationship is characterized a first factor k1 and second factor k2.

18. The method of claim 17, wherein the first optimized pulse-rate is calculated the according to the total energy available from a power supply to the pulser and probe circuit and the relationship between the total energy and the pulse repetition rate (PRF), which is:

$$P_{total} = \frac{V^2}{Z_{eq}} * PulseWidth * PRF * N_{ch}$$

wherein,
PulseWidth is the pulse width given as part of the operational setup;
Nch is the number of active elements of the respective pulser;
V is the voltage measured at a power supply 30 of the pulser circuit;
$Z_{eq}$ is the adaptive equivalent impedance of the pulser circuit.

19. The method of claim 18, wherein the second optimized pulse repetition rate is calculated according to the allowed power consumption within the pulser circuit and the relationship between the pulser circuit energy consumption and the pulse repetition rate (PRF), which is:

$$P_{pulser} = \left( \frac{V^2}{Z_{eq}} - \frac{V_{transducer}^2}{Z_{transducer}} \right) * PulseWidth * PRF * N_{ch}$$

wherein,
PulseWidth is the pulse width given as part of the operational setup;
Nch is the number of active elements of the respective pulser;
V is the voltage measured at a power supply 30 of the pulser circuit, $V_{transducer}$ is the voltage measured between probe circuit and pulser circuit;
$Z_{eq}$ is the adaptive equivalent impedance of the pulser circuit, $Z_{transducer}$ is the adaptive impedance of the respective probe.

\* \* \* \* \*